United States Patent [19]

Weber et al.

[11] Patent Number: 5,030,745
[45] Date of Patent: Jul. 9, 1991

[54] REACTION PRODUCTS OF 2-(AMINOETHYL)-AMINOPROPYL-ALKOXY SILANES AND CHLOROSILANES

[75] Inventors: Wilhelm Weber; Karl-Heinz Sockel, both of Leverkusen; Volker Wiskamp, Darmstadt; Jörg Jeremias, Bergisch Gladbach, all of Fed. Rep. of Germany

[73] Assignee: Bayer Aktiengesellschaft, Leverkusen, Fed. Rep. of Germany

[21] Appl. No.: 468,240

[22] Filed: Jan. 22, 1990

[30] Foreign Application Priority Data

Feb. 4, 1989 [DE] Fed. Rep. of Germany ....... 3903339

[51] Int. Cl.$^5$ ................................................ C07F 7/10
[52] U.S. Cl. ..................................................... 556/407
[58] Field of Search ......................................... 556/407

[56] References Cited

U.S. PATENT DOCUMENTS

| 3,170,941 | 2/1965 | Speier | 556/407 |
| 3,355,424 | 11/1967 | Brown | 260/46.5 |
| 3,509,194 | 4/1970 | Fink | 556/407 |
| 4,584,393 | 4/1986 | Webb et al. | 556/407 |
| 4,691,038 | 9/1987 | Pohl et al. | 556/407 |

FOREIGN PATENT DOCUMENTS 2032432  2/1971  Fed. Rep. of Germany ...... 556/407 UX
1162772  8/1969  United Kingdom ........ 556/407 UX

*Primary Examiner*—Paul F. Shaver
*Attorney, Agent, or Firm*—Connolly and Hutz

[57] ABSTRACT

Materials useful as bonding agents for silicone 1K-and 2K-sealing compositions are the reaction products of 2-(aminoethyl) -aminopropyl-alkoxy silanes of the following formula:

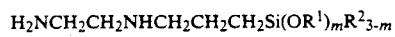

with chlorosilanes of the following formula:

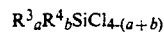

wherein
R$^1$, R$^2$, R$^3$ and R$^4$, independent of each other, are alkyl having 1 to 8 carbon atoms, cycloalkyl having 3 to 8 carbon atoms, alkenyl having 2 to 8 carbon atoms or cycloalkenyl having 3 to 8 carbon atoms;
m is 2 or 3,
a and b are 0, 1 or 2 and the sum of a and b is 0, 1 or 2.

3 Claims, No Drawings

REACTION PRODUCTS OF 2-(AMINOETHYL)-AMINOPROPYL-ALKOXY SILANES AND CHLOROSILANES

This invention relates to reaction products of 2-(aminoethyl)aminopropyl-alkoxy silanes and chlorosilanes containing at least two chlorine atoms on the silicon atom and to their use as bonding agent in 1K-RTV and 2K-RTV sealing materials based on silicones, polyurethanes or polyethers (so called modified silicones).

One conventional method of linking Si-N bonds is the condensation of chlorosilanes with dialkylamines accompanied by the elimination of HCl in accordance with the following equation:

$$R_3SiCl + HNR_2 \rightarrow R_3Si-NR_2 + HCl$$

(R=organic groups).

Chlorosilanes containing more than one chlorine atom on the silicon atom are capable of reacting analogously with equivalent quantities of dialkylamines to form compounds containing more than one Si-N bond in accordance with the following equation:

$$R_{4-x}SiCl_x + X\ HNR_2 \rightarrow R_{4-x}Si(NR_2)_x + X\ HCl$$

One special case of this reaction is the reaction of dichlorosilanes with N,N'-dialkyl-ethylene diamine to form diazasila-cyclopentanes:

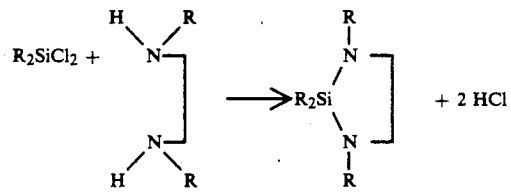

Reactions of dichlorosilanes with ethylene diamine also lead to compounds containing diaza-silacyclopentane units. As these units have two more condensable amine hydrogen atoms than N,N'-dialkyl-ethylene diamines, they can be joined together through $R_2Si$ groups to form polymers in accordance with the following equation:

$$nR_2SiCl_2 + nH_2NCH_2CH_2NH_2 \longrightarrow$$

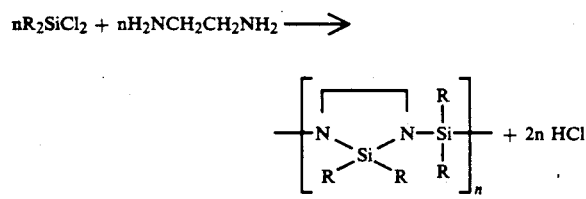

(see W. Fink, Helv. Chim. Acta, 50, 1131 (1967)).

The reactions of the above mentioned amines with chlorosilanes are carried out in the presence of an acid acceptor. The acid acceptor may consist of an excess of the amine which is to undergo reaction or it may consist of other bases, e.g. amine bases such as triethylamine.

The present invention relates to reaction products of 2-(aminoethyl)-aminopropyl-alkoxy silanes corresponding to the following general formula:

$$H_2NCH_2CH_2NHCH_2CH_2CH_2Si(OR^1)_m R^2_{3-m}$$

wherein
$R^1$ and $R^2$ = alkyl, cycloalkyl, alkenyl or cycloalkenyl (in each case with 1 to 8 carbon atoms), and
$R^1$ and $R^2$ may be identical or different and m may have the value 2 or 3
with chlorosilanes corresponding to the following general formula:

$$R^3_a R^4_b SiCl_{4-(a+b)}$$

wherein
$R^3$ and $R^4$ = alkyl, cycloalkyl, alkenyl, cycloalkenyl, alkoxy or aryl (in each case with 1 to 8 carbon atoms) and
$R^3$ and $R^4$ may be identical or different, a and b may assume the values 0, 1 or 2 and the sum of a+b is 0, 1 or 2.

The chlorine-free products all contain the following structural elements:

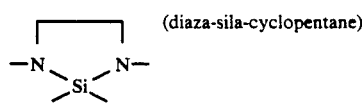 (diaza-sila-cyclopentane)

and

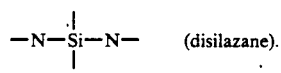 (disilazane).

The following are specific examples of suitable 2-(aminoethyl)-aminopropyl-alkoxy silanes:
$H_2NCH_2CH_2NHCH_2CH_2CH_2-Si(OCH_3)_3$
$H_2NCH_2CH_2NHCH_2CH_2CH_2-Si(OCH_3)_2CH_3$
$H_2NCH_2CH_2NHCH_2CH_2CH_2-Si(OC_2H_5)_3$
$H_2NCH_2CH_2NCH_2CH_2CH_2-Si(OC_2H_5)_2CH_3$
$H_2NCH_2CH_2NCH_2CH_2CH_2-Si(OCH_3)_2C_2H_5$
$H_2NCH_2CH_2NCH_2CH_2CH_2-Si(OC_2H_5)_2C_2H_5$
$H_2NCH_2CH_2NCH_2CH_2CH_2-Si(OC_3H_7)_3$
$H_2NCH_2CH_2NCH_2CH_2CH_2-Si(OC_3H_7)_2CH_3$
$H_2NCH_2CH_2NCH_2CH_2CH_2-Si(OC_3H_7)_2C_2H_5$ The following are particularly suitable chlorosilanes:
$SiCl_4$
$CH_3SiCl_3$
$C_2H_5SiCl_3$
$C_3H_7SiCl_3$
$C_2H_3SiCl_3$
$C_6H_5SiCl_3$
$C_6H_{11}SiCl_3$
$CH_3OSiCl_3$
$C_2H_5OSiCl_3$
$C_3H_7OSiCl_3$
$C_4H_9OSiCl_3$
$(CH_3)_2SiCl_2$
$(C_2H_5)_2SiCl_2$
$(C_3H_7)_2SiCl_2$
$(C_2H_3)_2SiCl_2$
$(C_6H_5)_2SiCl_2$
$(C_6H_{11})_2SiCl_2$
$(CH_3O)_2SiCl_2$
$(C_2H_5)_2SiCl_2$
$(C_3H_7O)_2SiCl_2$ $(C_4H_9O)_2SiCl_2$
$(CH_3)(C_2H_5)SiCl_2$
$(CH_3)(C_3H_7)SiCl_2$
$(C_2H_5)(C_3H_7)SiCl_2$
$(CH_3)(C_2H_3)SiCl_2$
$(CH_3)(C_6H_5)SiCl_2$
$(C_2H_5)(C_6H_5)SiCl_2$
$(C_2H_5)(C_2H_3)SiCl_2$
$(C_6H_5)(C_2H_3)SiCl_2$
$(CH_3)(CH_{30})SiCl_2$
$(CH_3)(C_2H_5O)SiCl_2$
$(CH_3)(C_3H_7O)SiCl_2$
$(CH_3)(C_4H_9O)SiCl_2$
$(C_2H_5)(CH_3O)SiCl_2$
$(CH_2H_5)(C_2H_5O)SiCl_2$
$(C_2H_5)(C_3H_7O)SiCl_2$
$(C_2H_5)(C_4H_9O)SiCl_2$
$(C_6H_5)(CH_3O)SiCl_2$
$(C_6H_5)(C_2H_5O)SiCl_2$
$(C_6H_5)(C_3H_7O)SiCl_2$
$(C_6H_5)(C_4H_9O)SiCl_2$
$(C_2H_3)(CH_3O)SiCl_2$
$(C_2H_3)(C_2H_5O)SiCl_2$
$(C_2H_3)(C_4H_9O)SiCl_2$ The reaction of dimethyl dichlorosilane with 2-(aminoethyl)aminopropyl-trimethoxy silane, for example, leads to a product mixture composed of 75% of

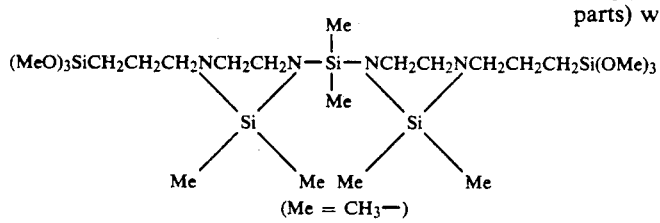

$(Me = CH_3-)$ and approximately 12% of

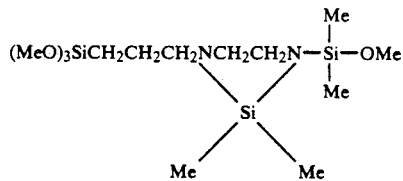

This product may be separated from the main product by distillation (see Example 1).

When the chlorine free reaction product of silicon tetrachloride and 2-(aminoethyl)-aminopropyl-trimethoxy silane has been worked up, it is found to have a composition corresponding to the stoichiometric proportions of the reaction and to be cross-linked.

It was surprisingly found that the reaction products according to the invention of 2-(aminoethyl)-aminopropylalkoxy silanes and chlorosilanes are suitable for use as bonding agents for 1K- and 2K-sealing materials based on silicones and polyurethanes or polyethers (so called modified silicones).

They have the advantage that by virtue of their high molecular weight and polymeric character they do not evaporate from the sealing materials, i.e. the sealing materials are odourless.

Another advantage is that they impart excellent storage stability, for example to RTV-1K-methoxy silicone pastes (see Example 2).

The invention will now be described in more detail with the aid of the following examples, in which parts and percentages denote parts by weight and percentages by weight.

EXAMPLE 1

Reaction of 2-(aminoethyl)-aminopropyl-trimethoxy silane with dimethyl-dichlorosilane.

97 parts of dimethyl dichlorosilane were added dropwise at room temperature in the course of 1.5 hours to a solution of 167 parts of 2-(aminoethyl)-aminopropyl-trimethoxy silane and 167 parts of triethylamine in 400 parts of hexane. The temperature rose to 60° C. during this addition. The reaction mixture was then stirred for 2 hours at room temperature, left to stand overnight and again boiled for 2 hours under reflux. The precipitated solid was filtered off and washed twice, in each case with 40 parts of hexane. The filtrate was then heated to temperatures of up to 60° C. at 5 mbar. The residue (185 parts) was characterised by the following GC/MS and $^{29}$Si-NMR values:

| | |
|---|---|
| $M^+ = 612$; about 75 vol. % | |
| $M^+ = 366$; about 12 vol. % | |
| 7.7 ppm (33 mol %) = | 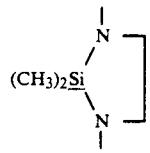 |
| −3.3 ppm (14 mol %) = | 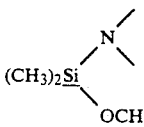 |
| −9.3 ppm (3 mol %) = <br> −10.6 ppm (10 mol %) | 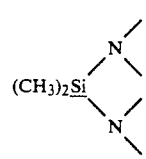 |
| −42.7 ppm (40 mol %) = | $-CH_2\underline{Si}(OCH_3)_3$ |

The product is virtually free from chlorine (found: 0.07% Cl).

EXAMPLE 2

5 parts by weight of a polydimethylsiloxane containing —OSi(OCH₃)₂CHhd—end groups and having a viscosity of 50 Pa.s were mixed in a planet mixer with 29 parts by weight of a polymethylsiloxane containing —OSi(CH₃)₃ end groups (viscosity 0.1 Pa.s) and 9.5 parts by weight of a pyrogenic silica. 0.5 parts by weight of methyl trimethoxy silane were then added. The reaction mixture was completed by the addition of 1.0 part by weight of the product from Example 1 and 0.3 parts by weight of (C₄H₉)₂Sn[OCOCH(C₂H₅)C₄H₉]₂. The paste was spread out to form a test sheet 2 mm in thickness for assessing the mechanical properties and was cured for 14 days at 23° C. and 50% relative humidity and then tested according to DIN 53 504:

Tensile strength: 2.03 MPa
E modulus 100%: 0.41 MPa
Elongation at break: 660%

To assess the tendency to cross-linking and the bonding properties, a test sheet 4 mm in thickness was applied to a glass plate over an area of 40×60 mm. After 24 hours, the material had cured right down to the glass surface and could no longer be pulled away from the surface without being torn due to the cohesive forces.

The storage stability of the uncured paste was assessed by means of a rapid test in which the sealing material was introduced into tubes and stored at 100° C. The material still cross-linked to a usable elastomer after up to 28 days storage.

What is claimed is:

1. Product containing diaza-sila-cyopentane groups and disilazane groups obtained from reaction of 2-(aminoethyl)-aminopropyl-alkoxy silanes of the following formula:

$$H_cNCH_2CH_2NHCH_2CH_2Si(OR^1)_mR^2{}_{3-m}$$

with chlorosilanes of the following formula:

$$R^3{}_aR^4{}_bSiCl_{4-(a+b)}$$

wherein
R¹, R², R³ and R⁴, indiependent of each other, are alkyl having 1 to 8 carbon atoms, cycloalkyl having 3 to 8 carbon atoms, alkenyl having 2 to 8 carbon atoms or cycloalkenyl having 3 to 8 carbon atoms;
m is 2 or 3,
a and b are 0, 1 or 2 and the sum of a and b is 0, 1 or 2.

2. Reaction products as claimed in claim 1 wherein the chlorosilane reactant is dimethyl dichlorosilane.

3. Reaction products as claimed in claim 1 wherein the alkoxy silane reactant is 2-(aminoethyl)-aminopropyl-trimethoxy silane.

* * * * *